United States Patent
Chang et al.

(10) Patent No.: US 9,155,716 B2
(45) Date of Patent: *Oct. 13, 2015

(54) ENHANCED BIMATOPROST OPHTHALMIC SOLUTION

(71) Applicant: ALLERGAN, INC., Irvine, CA (US)

(72) Inventors: Chin-Ming Chang, Tustin, CA (US); James N. Chang, Newport Beach, CA (US); Rhett M. Schiffman, Laguna Beach, CA (US); R. Scott Jordan, Trabuco Canyon, CA (US); Joan-En Chang-Lin, Tustin, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/826,047

(22) Filed: Mar. 14, 2013

(65) Prior Publication Data

US 2013/0197093 A1 Aug. 1, 2013

Related U.S. Application Data

(63) Continuation of application No. 13/551,362, filed on Jul. 17, 2012, which is a continuation of application No. 13/254,543, filed as application No. PCT/US2010/026151 on Mar. 4, 2010, application No. 13/826,047, which is a continuation of application No. 12/351,383, filed on Jan. 9, 2009, now Pat. No. 8,338,479, which is a continuation of application No. 11/083,261, filed on Mar. 16, 2005, now Pat. No. 7,851,504.

(60) Provisional application No. 61/157,225, filed on Mar. 4, 2009.

(51) Int. Cl.
| | | |
|---|---|---|
| *A61K 31/164* | (2006.01) | |
| *A61K 9/00* | (2006.01) | |
| *A61K 9/08* | (2006.01) | |
| *A61K 31/14* | (2006.01) | |
| *A61K 31/5575* | (2006.01) | |
| *A61K 47/18* | (2006.01) | |
| *A61K 31/165* | (2006.01) | |

(52) U.S. Cl.
CPC ............ *A61K 31/164* (2013.01); *A61K 9/0048* (2013.01); *A61K 9/08* (2013.01); *A61K 31/14* (2013.01); *A61K 31/165* (2013.01); *A61K 31/5575* (2013.01); *A61K 47/186* (2013.01)

(58) Field of Classification Search
CPC . A61K 2300/00; A61K 47/186; A61K 31/14; A61K 31/165; A61K 31/164; A61K 31/5575; A61K 9/08; A61K 9/0048
USPC ........................................................ 514/622
See application file for complete search history.

(56) References Cited

U.S. PATENT DOCUMENTS

| | | |
|---|---|---|
| 4,055,602 A | 10/1977 | Nelson |
| 4,100,192 A | 7/1978 | Morozowich |
| 4,122,282 A | 10/1978 | Nelson |
| 4,123,441 A | 10/1978 | Johnson |
| 4,128,577 A | 12/1978 | Nelson |
| 4,171,331 A | 10/1979 | Biddlecom |
| 4,183,870 A | 1/1980 | Caton |
| 4,303,796 A | 12/1981 | Nelson |
| 4,382,953 A | 5/1983 | Ishii |
| 4,543,353 A | 9/1985 | Faustini |
| 4,599,353 A | 7/1986 | Bito |
| 4,812,457 A | 3/1989 | Narumiya |
| 4,994,274 A | 2/1991 | Chan |
| 5,034,413 A | 7/1991 | Chan |
| 5,281,591 A | 1/1994 | Burke |
| 5,352,708 A | 10/1994 | Woodward |
| 5,474,979 A | 12/1995 | Ding |
| 5,510,383 A | 4/1996 | Bishop |
| 5,545,665 A | 8/1996 | Burk |
| 5,587,391 A | 12/1996 | Burk |
| 5,607,978 A | 3/1997 | Woodward |
| 5,688,819 A | 11/1997 | Woodward |
| 6,277,829 B1 * | 8/2001 | Asero et al. ............ 514/29 |
| 6,403,649 B1 | 6/2002 | Woodward |
| 6,596,765 B2 | 7/2003 | Ueno |
| 6,646,001 B2 | 11/2003 | Hellberg |
| 6,743,439 B1 | 6/2004 | Castillo |
| 6,933,289 B2 | 8/2005 | Lyons |
| 7,851,504 B2 | 12/2010 | Chang |

(Continued)

FOREIGN PATENT DOCUMENTS

| | | |
|---|---|---|
| CA | 2144967 | 3/1994 |
| CA | 2498233 | 3/2004 |

(Continued)

OTHER PUBLICATIONS

Louis Cantor, Bimatoprost: A Member of a New Class of Agents, the Prostamides, for Glaucoma Management, 10 Exp. Opin. Invest. Drugs 721 (2001).*
Robert Laibovitz, et al, Comparison of the Ocular Hypotensive Lipid AGN 192024 With Timolol, 119 Arch. Ophthalmol. 994 (Jul. 2001).*
Ciro Costagliola, et al, Ocular Surface Changes Induced by Topical Application of Latanoprost and Timolol: A Short-Term Study in Glaucomatous Patients With and Without Allergic Conjunctivitis, 239 Arch. Clin. Exp. Ophthalmol. 809 (2001).*
Alcon Laboratories, Inc., Travatan® (Travoprost Ophthalmic Solution) 0.004% Sterile, 2004, 7 Pages, NDA 21-257.
Alm, Albert et al, Uveoscleral Outflow—A Review, Experimental Eye Research, 2009, 760-768, 88(4).

(Continued)

*Primary Examiner* — Sean Basquill
(74) *Attorney, Agent, or Firm* — Lorenz Siddiqi (57) ABSTRACT

A composition comprising from 0.005% to 0.02% bimatoprost by weight and from 100 ppm to 250 ppm benzalkonium chloride, wherein said composition is an aqueous liquid which is formulated for ophthalmic administration is disclosed herein. A method which is useful in treating glaucoma or ocular hypertension related thereto is also disclosed herein.

12 Claims, 1 Drawing Sheet

(56) References Cited

U.S. PATENT DOCUMENTS

| | | | |
|---|---|---|---|
| 8,017,655 B2 | 9/2011 | Woodward | |
| 8,278,353 B2* | 10/2012 | Chang et al. | 514/530 |
| 8,299,118 B2* | 10/2012 | Chang et al. | 514/530 |
| 2002/0013294 A1* | 1/2002 | DeLong et al. | 514/79 |
| 2002/0103255 A1 | 8/2002 | Hellberg | |
| 2002/0177625 A1* | 11/2002 | O'Donnell et al. | 514/569 |
| 2004/0029771 A1 | 2/2004 | Rigdon | |
| 2004/0079671 A1* | 4/2004 | Bandyopadhyay et al. | 206/528 |
| 2004/0115234 A1 | 6/2004 | Gewirtz | |
| 2005/0004074 A1 | 1/2005 | Lyons | |
| 2005/0276867 A1 | 12/2005 | Lyons | |
| 2006/0141049 A1* | 6/2006 | Lyons et al. | 424/489 |
| 2006/0211770 A1 | 9/2006 | Chang | |
| 2009/0149546 A1 | 6/2009 | Chang | |
| 2011/0124737 A1 | 5/2011 | Chang | |
| 2012/0316243 A1* | 12/2012 | Chang et al. | 514/613 |

FOREIGN PATENT DOCUMENTS

| | | |
|---|---|---|
| DE | 2721534 | 12/1977 |
| EP | 0093380 | 11/1983 |
| EP | 0102230 | 3/1984 |
| EP | 0098141 | 11/1984 |
| EP | 0253094 | 1/1988 |
| EP | 0364417 | 4/1990 |
| EP | 0453127 | 10/1991 |
| FR | 2239458 | 7/1973 |
| FR | 2312240 | 12/1976 |
| FR | 2386523 | 11/1978 |
| FR | 2402644 | 4/1979 |
| JP | S49-069636 | 7/1974 |
| JP | S62-215537 | 9/1987 |
| JP | 2004-002358 | 1/2004 |
| LU | 68940 | 12/1973 |
| WO | 90-02553 | 3/1990 |
| WO | 92-08465 | 5/1992 |
| WO | 94-06433 | 3/1994 |
| WO | 02-07731 | 1/2002 |
| WO | 03-074038 | 9/2003 |
| WO | 2004-013119 | 2/2004 |
| WO | 2008-006235 | 1/2008 |

OTHER PUBLICATIONS

Answer, Defenses and Counterclaims of Defendants Apotex Inc. and Apotex Corp., Civil Action No. 10-CV-681, *Allergan, Inc. and Duke University v. Apotex Inc. and Apotex Corp.*, 20 pages (Nov. 22, 2010).
Arndt, H.C., The Synthesis and Biological Activity of Prostaglandin Analogs Containing Spirocyclic Rings, Prostaglandins, 1977, 837-843, 13 (5).
Ashton, Paul et al, Formulation Influence on Conjunctival Penetration of Four Beta Blockers in the Pigmented Rabbit: A Comparison with Corneal Penetration, Pharmaceutical Research, 1991, 1166-1174, 8 (9).
Bean, Gerald, Commercially Available Prostaglandin Analogs for the Reduction of Intraocular Pressure: Similarities and Differences, Survey of Ophthalmology, 2008, S69-S84, 53 (Supp. 1).
Berglund, Barbara et al, Investigation of Structural Analogs of Prostaglandin Amides for Binding to and Activation of CB1 and CB2 Cannabinoid Receptors in Rat Brain and Human Tonsils, Adv Exp Med Biol, 1999, 527-533, 469.
Bito, L.Z. et al, The Ocular Pharmacokinetics of Eicosanoids and Their Derivatives. 1. Comparison of Ocular Eicosanoid Penetration and Distribution Following the Topical Application of PGF2α, PGF2α-1-methyl Ester, and PGF2α-1-Isopropyl Ester, Exp. Eye Res., 1987, 217-226, 44.
Bito, LZ et al, Prostaglandins, Other Eicosanoids, and Their Derivatives as Potential Antiglaucoma Agents, Glaucoma: Applied Pharmacology in Medical Treatment, 1984, 477-505.
Bito, LZ, Biological Protection with Prostanoids, CRC Press, Inc., 1985, 231-252, 1, Cohen, M. M., ed., Boca Raton, Fla., CRC Press Inc.
Bito, LZ, Prostaglandins, Old Concepts and New Perspectives, Archives of Opthalmology, 1987, 1036-1039, 105.
Boyd, James, Quantitative Comparison of Methods of Administering Physostigmine, Archives Ophthalmology, 1943, 521-525, 30(4).
Brown, Michael, Control of Contamination in Ophthalmic Solutions, Proc. R. Sco. Med., 1967, 354-357, 60.
Brubaker, Richard et al, Effects of AGN 192024, a new Ocular Hypotensive Agent, on Aqueous Dynamics, American journal of Ophthalmology, 2001, 19-24, 131(1).
Burstein, Neal, Electrophysiologic and Morphologic Effects of Ophthalmic Preparations on Rabbit Cornea Epithelium, Invest Ophthalmol Visual Sci, 1977, 899-911, 16 (10).
Burstein, Neal, Preservative Alteration of Corneal Permeability in Humans and Rabbits, Investigative Ophthalmology & Visual Science, Dec. 1984, 1453-1457, 25(12).
Burstein, Neal, Preservative Cytotoxic Threshold for Benzalkonium Chloride and Chlorhexidine Digluconate in Cat and Rabbit Corneas, Invest. Ophthal. & Visual Sci., 1980, 308-313, 19 (3).
Cadet, Patrick et al, Molecular Identification and Functional Expression of μ3, a Novel Alternatively Spliced Variant of the Human μ Opiate Receptor Gene, J. Immunol., 2003, 5118-5123, 170.
Camber, Ola et al, Influence of Some Preservatives on the Corneal Permeability of Pilocarpine and Dexamethasone, in Vitro, International Journal of Pharmaceutics, 1987, 229-234, 39.
Camras, C.B., Reduction of Intraocular Pressure by Prostaglandins Applied topically to the Eyes of Conscious Rabbits, Investigative Ophthalmology & Visual Science, Dec. 1977, 1125-1134, 16(12), US.
Camras, Carl B. et al, Bimatoprost, the Prodrug of a Prostaglandin Analogue, Br J Ophthalmol, 2008, 862-863, 92.
Camras, Carl B. et al, Detection of the Free Acid of Bimatoprost in Aqueous Humor Samples From Human Eyes Treated with Bimatoprost Before Cataract Surgery, The American Academy of Ophthalmology, 2004, 2193-2198.
Camras, Carl B. et al, Reduction of Intraocular Pressure in Normal and Glaucomatous Primate (Aotus Trivirgatus) Eyes by Topically Applied Prostaglandin F2α, Current Eye Research, 1981, 205-209, 1 (4).
Camras, Carl et al, Intraocular Pressure Reduction with PhXA34, a New Prostaglandin Analogue, in Patients With Ocular Hypertension, Arch Ophthalmol, 1992, 1733-1738, 110.
Cantor, Louis et al, Levels of Bimatoprost Acid in the Aqueous Humour After Bimatoprost Treatment of Patients with Cataract, Br. J. Ophthalmol, 2007, 629-632, 91.
Cantor, Louis et al, Reply-Bimatoprost, the Prodrug of a Prostaglandin Analogue, Br J Ophthalmol, 2008, 863-864, 92.
Center for Drug Evaluation and Research, Summary Review of Application No. 22-184 (Lumigan 0.01%) (Jul. 2010).
Chang-Lin, Joan-En et al, Aqueous Humor Penetration of Topical Bimatoprost 0.01% and Bimatoprost 0.03% in Rabbits: Response to Authors, Clinical Ophthalmology, Aug. 9, 2011, 1119-1120, 5.
Cheng-Bennett, A. et al, Studies on a Novel Series of Acyl Ester Prodrugs of Prostaglandin F2α, British Journal of Ophthalmology, 1994, 560-567, 78.
Collin, Barry, Ultrastructural Changes to Corneal Stromal Cells Due to Ophthalmic Preservatives, ACTA Ophthalmologic, 1986, 72-78, 64.
Complaint for Patent Infringement: Civil Action No. 1:10-CV-681; *Allergan, Inc. and Duke University V. Apotex Inc. and Apotex Corp.*, 12 pages, Filed Sep. 8, 2010.
Costagliola, Ciro et al, Ocular Surface Changes Induced by Topical Application of Latanoprost and Timolol: A Short-Term Study in Glaucomatous Patients With and Without Allergic Conjunctivitis, Graefe's Arch Clin Exp Ophthalmol, 2001, 809-814, 239.
Crowston, Jonathan et al, Effect of Bimatoprost on Intraocular Pressure in prostaglandin FP Receptor Knockout Mice, Investigative Ophthalmology & Visual Science, 2005, 4571-4577, 46.
Curri, Joanne, Paragraph IV Letter to: Allergan, Inc. (Irvine, CA), Dec. 23, 2011, 12 Pages, Hi-Tech Pharmacal Co., Inc., Amityville, NY.
Davies, Sean, Hydrolysis of Bimatoprost (Lumigan) to Its Free Acid by Ocular Tissue In Vitro, Journal of Ocular Pharmacology and Therapeutics, 2003, 45-54, 19(1).

(56) References Cited

OTHER PUBLICATIONS

De Clercq, P., Cyclopentanones-VXL., Prostaglandin Synthesis Involving Catalytic Hydrogenation of 2,3-Dialkyl-4-Hydroxy-2-Cyclopentenones, Tetrahedron, 1976, 2747-2752, 32.
Deardorff, Dwight, Ophthalmic Preparation, Remington's Pharmaceutical Sciences, 1975, 1488, 15th ed.
Declaration of Larry Wheeler, Ph.D., 30 pages, Dec. 14, 2010.
Deluca, Patrick et al, Formulation of Small Volume Parenterals, Pharmaceutical Dosage Forms: Parenteral Medications, 1992, 173-248, 1.
Dubiner, Harvey, Efficacy and Safety of Bimatoprost in Patients With Elevated Intraocular Pressure: a 30-Day Comparison With Latanoprost, Surv. Ophthalmol, 2001, S353-S560, 45 (4).
Eisenberg, Dan, Bimatoprost and Travoprost: A Review of Recent Studies of Two New Glaucoma Drugs, Survey of Ophthalmology, 2002, S105-S115, 47 (1).
Faulkner, Robert, Aqueous Humor Concentrations of Bimatoprost Free Acid, Bimatoprost and Travoprost Free Acid in Cataract Surgical Patients administered Multiple Topical Ocular Doses of Lumigan or Travatan, Journal of Ocular Pharmacology and Therapeutics, 2010, 147-156, 26(2).
FDA Label for Approved NDA 22-184 of Lumigan 0.01% and Lumigan 0.03%, Aug. 31, 2010.
Frenkel, R E et al, Evaluation of Circadian Control of Intraocular Pressure After a Single Drop of Bimatoprost 0.03% or Travoprost 0.004%, Curr. Med. Res. Opin., Apr. 2008, 919-923, 24(4).
Gandolfi, Stefano, Three-month Comparison of Bimatoprost and Latanoprost in Patients With Glaucoma and Ocular Hypertension, Adv. Ther., 2001, 110-121, 18.
Gasset, Antonio et al, Benzalkonium Chloride Toxicity to the Human Cornea, American Journal of Ophthalmology, Aug. 1977, 169-171, 84(2).
Giuffre, Giuseppe, The Effects of Prostaglandin F2α in the Human Eye, Graefe's Archive Clin. & Exper. Ophthal., 1985, 139-141, 222.
Grass, George, Mechanisms of Corneal Drug Penetration I: In Vivo and In Vitro Kinetics, Journal of Pharmaceutical Sciences, Jan. 1988, 3-14, 77 (1).
Green, Keith, Influence of Various Agents on Corneal Permeability, American Journal of Ophthalmology, 1971, 897-905, 72.
Green, Keith, Prednisolone Phosphate Penetration Into and Through the Cornea, Investigative Ophthalmology, 1974, 316-319, 13 (4).
Green, Keith, The Effects of Preservatives on Corneal Permeability of Drugs, Biopharmaceutics of Ocular Drug Delivery, 1993, 43-59.
Handbook of Pharmaceutical Excipients, Monographs for Water, Sodium Phosphate, Sodium Chloride, and Citric Acid Monohydrate (1994).
Hecht, Gerald, Chapter 89: Ophthalmic Preparations, Remington: The Science and Practice of Pharmacy, 1995, 1563-1576, 2.
Hellberg, Mark et al, The Hydrolysis of the Prostaglandin Analog Prodrug Bimatoprost to 17-Phenyltrinor PGF2α by Human and Rabbit Ocular Tissue, J. Ocular Pharmacol. Ther., 2003, 97-103, 19(2).
Higaki, Kazutaka et al, Estimation and Enhancement of In Vitro Corneal Transport of S-1033, A Novel Antiglaucoma Medication, International Journal of Pharmaceutics, 1996, 165-173, 132, Elsevier, US.
Higginbotham, Eve et al., One-Year, Randomized Study Comparing Bimatoprost and Timolol in Glaucoma and Ocular Hypertension, Archives of Opthalmology, Oct. 2002, 1286-1293, 120 (10), US.
Ho, Norman et al, Physical Model Approach to the Design of Drugs with Improved Intestinal Absorption, Design of Biopharmaceutical Properties Through Prodrugs & Analogs, 1977, 136-227, Edward B. Roche ed.
Honohan, Thomas, Duration of Activity of the Acid, Methyl Ester and Amide of an Orally Active Platelet Aggregation Inhibitory Prostanoid in the Rat, Prostoglandins, 1980, 139, 19.
Huang, Andrew et al, Paracellular Permeability of Corneal and Conjunctival Epithelia, Investigative Ophthalmology & Visual Science, 1989, 684-689, 30(4).

Jordan, B.A. et al, G-Protein-Coupled Receptor Heterodimerization Modulates Receptor Function, Nature, Jun. 17, 1999, 697-700, 399(6737).
Katz, Jay et al, Comparison of Human Ocular Distribution of Bimatoprost and Latanoprost, Investigative Ophthalmology & Visual Science, Jul. 9, 2010, 1-28.
Katz, Jay, Twelve-Month, Randomized, Controlled Trial of Bimatoprost 0.01%, 0.0125%, and 0.03% in Patients with Glaucoma or Ocular Hypertension, Am J Ophthalmology, 2010, 661-671, 149(4).
Kaur, Indu Pal et al, Formulation and Evaluation of Ophthalmic Preparations of Acetazolamide, International Journal of Pharmaceutics, 2000, 119-127, 199.
Kaur, Indu Pal et al, Penetration Enhancer and Ocular Bioadhesives: Two New Avenues for Ophthalmic Drug Delivery, Drug Development and Industrial Pharmacy, 2002, 353-369, 28(4).
Keller, N. et al., Increased Corneal Permeability Induced by the Dual Effects of Transient Tear Film Acidification and Exposure to Benzalkonium Chloride, Experimental Eye Research, 1980, 203-210, 30.
Kibbe, Arthur, Benzalkonium Chloride, Handbook of Pharmaceutical Excipients, 2000, 33-35.
Laibovitz, Robert, Comparison of the Ocular Hypotensive Lipid Agn 192024 With Timolol, Arch Ophthal, 2001, 994, 119.
Lawrence, C.A., An Evaluation of Chemical Preservatives for Ophthalmic Solutions, J Am Pharm Assoc, 1955, 457, 44(8).
Lawrence, C.A., Chemical Preservatives for Ophthalmic Solutions, Am J Ophthal, 1955, 385, 39.
Lee, Vincent et al, Improved Ocular Drug Delivery with Prodrugs, Prodrugs: Topical and Ocular Drug Delivery, 1992, 221-297, Kenneth Sloan Edition.
Lee, Vincent et al, Review: Topical Ocular Drug Delivery: Recent Developments and Future Challenges, Journal of Ocular Pharmacology, 1986, 67-108, 2(1).
Liang, Y. et al, Identification and Pharmacological Characterization of the Prostaglandin FP Receptor and FP Receptor Variant Complexes, Br. J. Pharmacol., 2008, 1079-1093, 154.
Lumigan (Allergan) (Bimatoprost Ophthalmic Solution) 0.03% Product Monograph, 2001, 7 Pages.
Lumigan Package Insert, Mar. 2001, 6 Pages, NDA 21-275.
Lumigan® 0,1 mg/ml, 3 pages, Jan. 2010.
Lumigan® RC (Allergan) (Bimatoprost Ophthalmic Solution 0.01%), 2009, 7 Pages.
Lumigan, Product Description, Allergan, Inc., Jul. 2003, pp. 1-6.
Lumigan® monograph in the 57th PDR (2003).
Lyle, Donald, Early Ocular Manifestations in the Laurence-Moon-Biedl Syndrome, American Journal of Ophthalmology, 1946, 939-946, 29.
Madhu, Cherukury et al, Effect of Benzalkonium Chloride/EDTA on the Ocular Bioavailability of Ketorolac Tromethamine Following Ocular Instillation to Normal and De-epithelialized Corneas of Rabbits, Journal of Pharmaceutical Sciences, Apr. 1996, 415-418, 85(4).
Malhotra, Manjusha et al, Permeation Through Cornea, Indian Journal of Experimental Biology, Jan. 2001, 11-24, 39.
Martin, F.N., Preparation of Ophthalmic Solutions With Special Reference to Hydrogen Ion Concentration and Tonicity, Arch Ophthal, 1950, 561, 44.
Maurice, David, The Effect of the Low Blink Rate in Rabbits on Topical Drug Penetration, J Ocular Pharmacology and Therapeutics, 1995, 297-304, 11(3).
Maxey, Kirk, The Hydrolysis of Bimatoprost in Corneal Tissue Generates a Potent Prostanoid FP Receptor Agonist, Survey of Ophthalmology, 0812002, S34-S40, 47 (Supp. 1).
McPherson, Samuel, Self-Sterilizing Ophthalmic Solutions, Am J Ophthal, 1949, 675, 32.
Mealy, N.E., Ophthalmic Drugs, Drugs of the Future, 2002, 509-523, 27 (5).
Medical Review, Application No. 21-275, Center for Drug Evaluation and Research, 2001.
Miller, William et al, Biological Activities of 17-Phenyl-18, 19,20-Trinorprostaglandins, Prostaglandins, Jan. 1975, 9-18, 9(1).
Mitra, Ashim, Ophthalmic Drug Delivery Systems, Drugs and the Pharmaceutical Sciences, 2003, 6 Pages, 2nd Edition (vol. 130).

(56) References Cited

OTHER PUBLICATIONS

Mullen, William, Ophthalmic Preservatives and Vehicles, Surv Ophthal, 1973, 469, 17(6).

Nema, Sandeep et al, Excipients—Their Role in Parenteral Dosage Forms, Encyclopedia of Pharmaceutical Technology, 2002, 1164-1187, 2.

Nilsson, SIV, PGF 2α Increases Uveoscleral Outflow, Invest. Ophthalmol. Vis. Sci, 1987, 284, 28 (Suppl).

Noecker, Robert et al, Corneal and Conjunctival Changes Caused by Commonly Used Glaucoma Medications, Cornea, 2004, 490-496, 23.

Noecker, Robert, Bimatoprost/Latanoprost Study Group. A Six Month Randomized Clinical Trial Comparing the Intraocular Pressure Lowering Efficacy of Bimatoprost and Latanoprost in Patients With Ocular Hypertension or Glaucoma, Am J Ophthal, 2003, 55-63, 135.

Novack, Gary et al, Commercially Available Ocular Hypotensive Products: Preservative Concentration, Stability, Storage, and In-Life Utilization, Journal of Glaucoma, 2001, 483-486, 10.

O'Brien, C.S., Carbaminoyl-choline Chloride in the Treatment of Glaucoma Simplex, Arch Ophthal, 1942, 253, 27.

O'Brien, C.S., Doryl in the Treatment of Glaucoma Simplex, Tran Am Ophthal Soc, 1941, 175, 39.

Ogundele, Abayomi et al, Impact of Topical Bimatoprost 0.01% and Bimatoprost 0.03% on Conjunctival Irritation in Rabbits, Clinical Ophthalmology, Feb. 13, 2010, 77-80, 4.

Ogundele, Abayomi et al, In Vivo Comparative Study of Ocular Vasodilation, A Relative Indicator of Hyperemia, in Guinea Pigs Following Treatment With Bimatoprost Ophthalmic Solutions 0.01% and 0.03%, Clinical Ophthalmology, Jun. 19, 2010, 649-652, 4.

Okabe, Komei et al, Effect of Benzalkonium Chloride on Transscleral Drug Delivery, Investigative Ophthalmology & Visual Science, 2005, 703-708, 46.

Parrish, Richard, A Comparison of Latanoprost, Bimatoprost, and Travoprost in Patients With Elevated Intraocular Pressure: A 12-Week, Randomized, Masked Evaluator Multicenter Study, Am J Ophthalmol, 2003, 688-703, 135.

Pfeiffer, N, New Developments in Glaucoma Drug Therapy, Ophthalmologist, 1992, W1-W13, 89.

Pfister, Roswell, The Effects of Ophthalmic Drugs, Vehicles, and Preservatives on Corneal Epithelium: a Scanning Electron Microscope Study, Effects of Opthalmic Drugs, 1976, 246-259, 15 (4).

Pharmacia & Upjohn, Xalatan (Latanoprost Ophthalmic Solution), 1998, 2 Pages.

Physicians' Desk Reference, 2004, 553-554, 58th Edition.

Physicians' Desk Reference, 56th ed., pp. 212-213, 543, 553-554, 2864-2865 (2002).

Physicians' Desk Reference, 59th ed., pp. 555-556 (2005).

Pisella, Pierre-Jean, Conjunctival Proinflammatory and Proapoptotic Effects of Latanoprost and Preserved and Unpreserved Timolol: An Ex Vivo and In Vitro Study, Investigative Ophthalmology & Visual Science, 2004, 1360-1368, 45.

Podder, Samir, Improving the Safety of Topically Applied Timolol in the Pigmented Rabbit Through Manipulation of Formulation Composition, Exp. Eye Res., 1992, 747-757, 54.

Poyer, J.F. et al, Prostaglandin F2α Effects on Isolated Rhesus Monkey Ciliary Muscle, Invest. Ophthalmol. Vis. Sci., Nov. 1995, 2461-2465, 36(12).

Raymond Rowe et al, Handbook of Pharmaceutical Excipients, APha Publications, 2003, 4th edition.

Remington, The Science and Practice of Pharmacy, 20th ed. at 831 (2000).

Remington, The Science and Practice of Pharmacy, 21st ed. at 864 (2005).

Remington's Pharmaceutical Sciences 1501 (15th ed. 1975).

Response from the Food and Drug Administration to Pfizer's Citizen Petition and a Supplement at 23 (Exhibit 5), 27 pages (Aug. 31, 2010).

Resul, B et al, Phenyl-substituted Prostaglandins: Potent and Selective Antiglaucoma Agents, J. Med. Chem., Jan. 22, 1993, 243-248, 36(2).

Robin, Alan et al, An Accurate Comparison of Bimatoprost's Efficacy and Adverse Effects, Arch Ophthalmol, Jul. 2002, 999-1000, 120.

Roggeband, R., Eye Irritation in Rabbit and Man After Single Applications of Equal Volumes of Undiluted Model Liquid Detergent Products, Food & Chem Toxic, 2000, 727, 38.

Romano, Maria Rosaria et al, Evidence for the Involvement of Cannabinoid DB1 Receptors in the Bimatoprost-Induced Contractions on the Human Isolated Ciliary Muscle, Investigative Ophthalmology & Visual Science, Aug. 2007, 3677-3382, 48(8).

Sandoz Paragraph IV Letter, Jul. 11, 2011, 19 Pages.

Sasaki, Hitoshi et al, Different Effects of Absorption Promoters on Corneal and Conjunctival Penetration of Ophthalmic Beta-Blockers, Pharmaceutical Research, 1995, 1146-1150, 12(8).

Sasaki, Hitoshi et al, Enhancement of Ocular Drug Penetration, Critical Reviews in Therapeutic Drug Carrier Systems, 1999, 85-146, 16(1).

Sasaki, Hitoshi et al, Ophthalmic Preservatives as Absorption Promoters for Ocular Drug Delivery, J. Pharm. Pharmacol., 1995, 703-707, 47, US.

Sasaki, Hitoshi, Modification of Ocular Permeability of Peptide Drugs by Absorption Promoters, Biol Pharm Bull, 2000, 1524, 23(12).

Sasaki, Hitoshi, Ocular Permeability of FITC-Dextran with Absorption Promoter for Ocular Delivery of Peptide Drug, J Drug Target, 1995, 129, 3.

Scholz, Martina, Pilocarpine Permeability Across Ocular Tissues and Cell Cultures: Influence of Formulation Parameters, Journal of Ocular Pharmacology and Therapeutics, 2002, 455-468, 18 (5).

Schumer, Robert et al, Medical Treatment of Glaucoma, Current Opinion in Ophthalmology, 1991, 140-150, 2.

Sharif, N.A. et al, Cat Iris Sphincter Smooth-Muscle Contraction: Comparison of FP-Class Prostaglandin Analog Agonist Activities, J. Ocul. Pharmacol. Ther., Apr. 2008, 152-163, 24(2).

Sharif, N.A. et al, Human Ciliary Muscle Cell Responses to FP-class Prostaglandin Analogs: Phosphoinositide Hydrolysis, Intracellular Ca2+ Mobilization and MAP Kinase Activation, J. Ocul. Pharmacol Ther., 2003, 437-455, 19.

Sharif, N.A. et al, Human Trabecular Meshwork cell Responses Induced by Bimatoprost, Travoprost, Unoprostone, and Other FP Prostaglandin Receptor Agonist Analogues, Invest. Ophthalmol Vis. Sci., 2003, 715-721, 44.

Sharif, N.A. et al, Ocular Hypotensive FP Prostaglandin (PG) Analogs: PG Receptor Subtype Binding Affinities and Selectivities, and Agonist Potencies at FP and Other PG Receptors in Cultured Cells, Journal of Ocular Pharmacology and Therapeutics, 2003, 501-515, 19(6).

Sharif, N.A. et al, Update and Commentary on the Pro-Drug Bimatoprost and a Putative Prostamide Receptor, Expert Rev. Ophthalmol., 2009, 477-489, 4(5).

Sjoquist, Birgitta et al, Ocular and Systemic Pharmacokinetics of Latanoprost in Humans, Surv. Ophthalmol., Aug. 2002, S6-S12, 47(Suppl 1).

Sjoquist, Birgitta et al, Pharmacokinetics of Latanoprost in the Cynomolgus Monkey. 3rd Communication: Tissue Distribution After Topical Administration on the Eye Studied by Whole Body Autoradiography, Glaucoma Research Laboratories. Arzneim-Forsch/Drug Res., 1999, 240-249, 49.

Skolaut, Milton, Ophthalmic Medication, Bull Am Soc Hosp Pharm, 1948, 172, 5(4).

Spada, C.S. et al, Bimatoprost and Prostaglandin F2α Selectively Stimulate Intracellular Calcium Signaling in Different Cat iris Sphincter Cells, Exp. Eye Res., Jan. 2005, 135-145, 80(1).

Stamer, W.D. et al, Cellular Basis for Bimatoprost Effects on Human Conventional Outflow, Invest. Ophthalmol. Vis. Sci., Oct. 2010, 5176-5181, 51(10).

Starr, Michael, Further Studies on the Effects of Prostagladin on Intraocular Pressure in the Rabbit, Exp. Eye Res., 1971, 170-177, 11.

(56) References Cited

OTHER PUBLICATIONS

Stern, F.A., Comparison of the Hypotensive and Other Ocular Effects of Prostaglandins E2 and F2α on Cat and Rhesus Monkey Eyes, Invest Ophthal Visual Sci, 1982, 588-598, 22.

Stewart, William, Corneal Punctate Staining with Latanoprost, Bimatoprost, and Travoprost in Healthy Subjects, J Glaucoma, 2003, 475-479, 12 (6).

Stjernschantz, Johan et al, From PGF2α-isopropyl Ester to Latanoprost: A Review of the Development of Xalatan: The Proctor Lecture, Invest. Ophthalmol. Vis. Sci., May 2001, 1134-1145, 42(6).

Stjernschantz, Johan, Studies on Ocular Inflammation and Development of a Prostaglandin Analogue for Glaucoma Treatment, Exp. Eye Res., Apr. 2004, 759-766, 78(4).

Swan, Kenneth, Reactivity of the Ocular Tissues to Wetting Agents, American Journal of Ophthalmology, 1944, 1118-1122, 27.

Tang-Liu, Diane, Effects of Four Penetration Enhancers on Corneal Permeability of Drugs in Vitro, Journal of Pharmaceutical Sciences, 1994, 85-90, 83 (1).

Thygesen, J., Short-term Effect of Latanoprost and Timolol Eye Drops on Tear Fluid and the Ocular Surface in Patients with Primary Open-Angle Glaucoma and Ocular Hypertension, Acta Ophthal Scand, 2000, 37-41, 78.

Tonjum, Asbjorn, Permeability of Rabbit Corneal Epithelium to Horseradish Peroxidase After the Influence of Benzalkonium Chloride, Acta Ophthalmologica, Jan. 22, 1975, 335-347, 53.

Travatan (travoprost ophthalmic solution) 0.004% Product Insert, NDA 21-257, Mar. 16, 2001, 7 Pages.

Van Alphen, G.W.H.M. et al, The effect of Prostaglandins on the Isolated Internal Muscles of the Mammalian Eye, Including Man, Documenta Ophthalmologica, 1977, 397-415, 42(4).

Van Der Bijl, Pieter, Effects of Three Penetration Enhancers on Transcorneal Permeation of Cyclosporine, Cornea, 2001, 505-508, 20 (5).

Vielhauer, G.A. et al, Cloning and Localization of hFP(S): a Six-Transmembrane mRNA Splice Variant of the Human FP Prostanoid Receptor, Arch Biochem Biophys., Jan. 15, 2004, 175-185, 421(2).

Walter, Modell, Pharmacologic Action of Some Ophthalmic Drugs, Arch Ophthal, 1947, 160, 37.

Walter, Thomas, 24-Hour IOP Control with Once-daily Bimatoprost, Timolol Gel-forming Solution, or Latanoprost: A 1-Month, Randomized, Comparative Clinical Trial, Survey of Ophthalmology, 2004, S26-S35, 49(1).

White, J.H. et al, Heterodimerization is Required for the Formation of a Functional GABA(B) Receptor, Nature, Dec. 17, 1998, 679-682, 396(6712).

Wilson, S.J. et al, Dimerization of the Human Receptors for Prostacyclin and Thromboxane Facilitates Thromboxane Receptor-Mediated CAMP Generation, J. Biol. Chem., Dec. 17, 2004, 53036-53047, 279(51).

Woodford, Roger, Penetration Enhancers and the Percutaneous Absorption of Drugs: An Update, J. Toxicol.—Cut. & Ocular Toxicol., 1986, 167-177, 5(3).

Woodward, David et al, Bimatoprost Effects on Aqueous Humor Dynamics in Monkeys, J. Ophthalmol., 2010, 5 pages.

Woodward, David et al, Bimatoprost: a Novel Antiglaucoma Agent, Cardiovascular Drug Reviews, 2004, 103-120, 22(2).

Woodward, David et al, Identification of an antagonist that selectively blocks the activity of prostamides (prostaglandin-ethanolamides) in the feline iris, British Journal of Pharmacology, 2007, 342-352, 150.

Woodward, David et al, The Pharmacology of Bimatoprost (LumiganTM), Surv Ophthalmol, 2001, S337-S345, Suppl 4.

Woodward, David, Pharmacological Characterization of a Novel Antiglaucoma Agent, Bimatoprost (AGN 192024), J. Pharmacol, Exp. Ther., Jan. 24, 2003, 772-785, 305 (2).

Xalatan® Eye Drops, Retrieval Date : Oct. 2, 2010, 3 pages, http://home.intekom.com/pharm/pharmaca/xalatan.html.

Xalatan® product information in the PDR 59th edition, p. 2762-2763/(2005).

Xu, Ke-Ping, Corneal Organ Culture Model for Assessing Epithelial Responses to Surfactants, Tox. Sci., 2000, 306, 58.

Yamaji, K. et al, Prostaglandins E1 and E2, but not F2α or Latanoprost, Inhibit Monkey Ciliary Muscle Contraction, Curr. Eye Res., Aug. 2005, 661-665, 30(8).

\* cited by examiner

ENHANCED BIMATOPROST OPHTHALMIC SOLUTION

CROSS-REFERENCE

This application is a Continuation of U.S. patent application Ser. No. 13/551,362, filed Jul. 17, 2012, which is a Continuation of U.S. patent application Ser. No. 13/254,543, filed Apr. 16, 2012, which is a U.S. National Stage Application under 35 U.S.C. §371 of PCT Patent Application No. PCT/US10/26151, filed Mar. 4, 2010, which claims the benefit of U.S. Provisional Patent Application Ser. No. 61/157,225, filed Mar. 4, 2009, and is also a continuation in part to U.S. patent application Ser. No. 12/351,383, filed Jan. 9, 2009, now U.S. Pat. No. 8,338,479, issued Dec. 25, 2012, which is a Continuation of U.S. patent application Ser. No. 11/083,261, filed Mar. 16, 2005, now U.S. Pat. No. 7,851,504, issued Dec. 14, 2010, each of which are incorporated herein by reference in their entirety.

BACKGROUND OF THE INVENTION

1. Field of the Invention

This invention relates to pharmaceutical compositions comprising bimatoprost.

2. Description of Related Art

Bimatoprost, shown below, is a prostamide marketed commercially for the treatment of glaucoma and ocular hypertension.

Formula I

Benzalkonium chloride (BAK) is a preservative used in many commercial ophthalmic products to prevent microbial contamination in multi-use products. The commercial eye drops (Bimatoprost, Allergan, Inc., Irvine, Calif.) contain 0.03% bimatoprost and 0.005% BAK. Although no other prostamides are currently marketed for the treatment of glaucoma, several prostaglandin analogs are commercially available which use BAK as a preservative. These include latanoprost (Xalatan), travoprost (Travatan), and unoprostone isopropyl (Rescula), which require significantly more BAK, from 150-200 ppm, to meet antimicrobial effectiveness tests in the United States and Europe.

U.S. Pat. No. 6,596,765 B2 discloses a composition comprising 0.005% or 0.0005% latanoprost and 0.2 mg/mL BAK.

U.S. Pat. No. 6,646,001 B2 discloses compositions comprising 0.03% bimatoprost and 0.01% BAK or "0.01%+5% excess" BAK.

DETAILED DESCRIPTION OF THE INVENTION

Composition comprising from 0.005% to 0.02% bimatoprost by weight and from 100 ppm to 250 ppm benzalkonium chloride are disclosed, wherein said composition is an aqueous liquid which is formulated for ophthalmic administration. Methods which are useful in treating glaucoma or ocular hypertension related thereto are also disclosed herein.

An aqueous liquid which is formulated for ophthalmic administration is formulated such that it can be administered topically to the eye. The comfort should be maximized as much as possible, although sometimes formulation considerations (e.g. drug stability) may necessitate less than optimal comfort.

In certain compositions, the concentration of bimatoprost is from 0.005% to 0.02% w/v. In other compositions the concentration of bimatoprost is from 0.01% to 0.02%. In other compositions, the concentration is 0.0125% or 0.015% bimatoprost.

In certain compositions the concentration of BAK is from 50 ppm to 200 ppm. In other compositions the concentration of BAK is from 100 ppm to 200 ppm. In other compositions the concentration of BAK is from 150 ppm to 250 ppm.

In ophthalmic compositions, a chelating agent may be used to enhance preservative effectiveness. Suitable chelating agents are those known in the art, and, while not intending to be limiting, edetate salts (EDTA) are useful chelating agents.

In certain compositions, concentration of EDTA is at least 0.001%. In other compositions, the concentration of EDTA is at least 0.01%. In other compositions, the concentration of EDTA is 0.15% or less. In other compositions, the concentration of EDTA is 0.1% or less. In other compositions, the concentration of EDTA is 0.05% or less.

As is known in the art, buffers are commonly used to adjust the pH to a desirable range for ophthalmic use. Generally, a pH of around 6-8 is desired, and in certain compositions a pH of 7.4 is desired. Many buffers including salts of inorganic acids such as phosphate, borate, and sulfate are known.

Another commonly used excipient in ophthalmic compositions is a viscosity-enhancing agent, or a thickening agent. Thickening agents are used for a variety of reasons, ranging from improving the form of the formulation for convenient administration to improving the contact with the eye to improve bioavailability. The viscosity-enhancing agent may comprise a polymer containing hydrophilic groups such as monosaccharides, polysaccharides, ethylene oxide groups, hydroxyl groups, carboxylic acids or other charged functional groups. While not intending to limit the scope of the invention, some examples of useful viscosity-enhancing agents are sodium carboxymethylcellulose, hydroxypropylmethylcellulose, povidone, polyvinyl alcohol, and polyethylene glycol.

In ophthalmic solutions, tonicity agents often are used to adjust the composition of the formulation to the desired isotonic range. Tonicity agents are well known in the art and some examples include glycerin, mannitol, sorbitol, sodium chloride, and other electrolytes.

One composition has a pH of 7.4 and consists essentially of 0.015% bimatoprost, 200 ppm benzalkonium chloride, from 0 to 0.03% EDTA, a phosphate buffer, NaCl, and water.

Another composition has a pH of 7.4 and comprises 0.02% bimatoprost, 200 ppm benzalkonium chloride, from 0 to 0.03% EDTA, a phosphate buffer, NaCl, and water.

Another composition has a pH of 7.4 and consists of 0.01% bimatoprost, 200 ppm benzalkonium chloride, from 0 to 0.03% EDTA, a phosphate buffer, NaCl, and water.

One embodiment comprises 0.01% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment comprises 0.0125% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment comprises 0.015% Bimatoprost, 0.02% Benzalkonium Chloride, 0.268% Sodium Phosphate Dibasic, Heptahydrate, 0.014% Citric Acid, Monohydrate, 0.81% Sodium Chloride, 0.03%, EDTA, and water, wherein the pH is 7.3.

Another embodiment comprises 0.02% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment comprises 0.005% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment consists essentially of 0.015% Bimatoprost, 0.01%-0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment consists of 0.015% Bimatoprost, 0.01%-0.02% Benzalkonium Chloride, 0.268% Sodium Phosphate Dibasic, Heptahydrate, 0.014% Citric Acid, Monohydrate, 0.81% Sodium Chloride, 0.03%, EDTA, and water, wherein the pH is 7.3.

Another embodiment consists essentially of 0.02% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment consists of 0.0125% Bimatoprost, 0.01%-0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment consists of 0.015% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment consists of 0.015% Bimatoprost, 0.02% Benzalkonium Chloride, 0.268% Sodium Phosphate Dibasic, Heptahydrate, 0.014% Citric Acid, Monohydrate, 0.81% Sodium Chloride, 0.03%, EDTA, and water, wherein the pH is 7.3.

Another embodiment consists of 0.02% Bimatoprost, 0.02% Benzalkonium Chloride, 0.268% Sodium Phosphate Dibasic, Heptahydrate, 0.014% Citric Acid, Monohydrate, 0.81% Sodium Chloride, EDTA and water, wherein the pH is 7.3.

One embodiment of the present invention is shown below:

Formulations containing 0.268% sodium phosphate dibasic heptahydrate, 0.014% citric acid, 0.83% sodium chloride, with the pH adjusted to 7.3 in qs water, and the amounts of bimatoprost, BAK, and EDTA listed in Table 1 below were prepared by conventional methods well known in the art.

TABLE 1

| Formulations |
| --- |
| 1. 0.03% Bimatoprost (50 ppm BAK) Control |
| 2. 0.03% Bimatoprost - 200 ppm BAK |
| 3. 0.03% Bimatoprost - 0.015% TPGS (no preservative) |
| 4. 0.03% Bimatoprost - 0.2% TPGS (no preservative) |
| 5. 0.03% Bimatoprost - 0.4% TPGS (no preservative) |
| 6. 0.03% Bimatoprost - 1.0% TPGS (no preservative) |

EXAMPLE 2

Studies were carried out to determine the effect of benzalkonium chloride (BAK) and d-alpha tocopheryl polyethylene glycol 1000 succinate (TPGS) on ocular absorption of bimatoprost in vivo. For the in vivo study, eighteen female rabbits were given a single 28 μL eyedrop bilaterally and aqueous humor samples were collected (n=3 animals with 6 eyes per formulation) at 60 min postdose. Two rabbits (4 eyes) remained untreated to serve as pre-dose bioanalytical controls. Bimatoprost and its parent carboxylic acid extracted from aqueous humor and in vitro samples were analyzed by a liquid chromatography tandem mass spectrometry (LC-MS/MS) method with a quantitation range of 0.25-60 ng/mL.

Due to extensive metabolism of bimatoprost in rabbit eyes, its parent acid was used as a surrogate for determining ocular absorption of bimatoprost. Concentration of the acid in rabbit aqueous humor following single dose of 6 different bimatoprost formulations are summarized in FIG. 1 and Table 2 below.

TABLE 2

Figure 1:
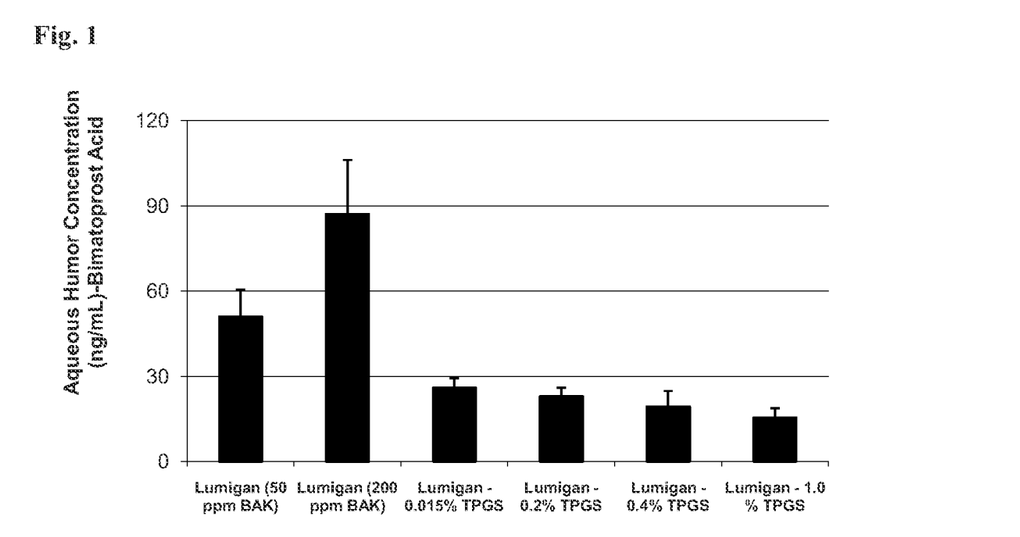
FIG. 1 is a plot showing the aqueous humor concentration of the parent acid of bimatoprost after topical administration of several formulations.

| Formulations | Aqueous Humor[a] (ng/mL) |
| --- | --- |
| 1. 0.03% Bimatoprost (50 ppm BAK) Control | 51.0 ± 9.4 |
| 2. 0.03% Bimatoprost - 200 ppm BAK | 87.2 ± 19.0* |
| 3. 0.03% Bimatoprost - 0.015% TPGS (no preservative) | 26.1 ± 3.3* |
| 4. 0.03% Bimatoprost - 0.2% TPGS (no preservative) | 22.9 ± 3.2* |
| 5. 0.03% Bimatoprost - 0.4% TPGS (no preservative) | 19.3 ± 5.6* |
| 6. 0.03% Bimatoprost - 1.0% TPGS (no preservative) | 15.4 ± 3.3* |

[a]Mean ± SD. Per formulation, N = 3 rabbits (6 eyes).
*Statistically different (p < 0.05) compared to 0.03% Bimatoprost

| Component | Concentration (% w/v) | Concentration (mg/mL) | Reference of Quality Standard | Function |
| --- | --- | --- | --- | --- |
| Bimatoprost | 0.01 | 0.1 | In-house standard | Drug Substance |
| Benzalkonium Chloride[a] | 0.02 | 0.2 | NF/Ph Eur | Preservative |
| Dibasic Sodium Phosphate Heptahydrate | 0.268 | 2.69 | USP | Buffering Agent |
| Citric Acid Monohydrate | 0.014 | 0.14 | USP/Ph Eur | Buffering Agent |
| Sodium Chloride | 0.81 | 8.1 | USP/Ph Eur | Tonicity Agent |
| Hydrochloric Acid[b] | Adjust pH to 7.3 | | NF/Ph Eur | pH Adjuster |
| Sodium Hydroxide[b] | | | NF/Ph Eur | pH Adjuster |
| Purified Water | q.s. ad 100 | q.s. ad 1 mL | USP/Ph Eur | Vehicle |

Test formulations containing 0.015%, 0.2%, 0.4% and 1.0% TPGS resulted in a lower aqueous humor carboxylic acid concentration compared to Bimatoprost by 52%, 59%, 62% and 72%, respectively. In contrast, 0.03% Bimatoprost containing 200 ppm BAK resulted in 57% higher aqueous humor AGN 191522 concentration compared to Bimatoprost (50 ppm BAK).

While not intending to limit the scope of the invention in any way, or be bound by theory, compared to the Bimatoprost control, formulations containing TPGS resulted in decrease bimatoprost permeability. In contrast, formulations with higher BAK resulted in higher permeability.

EXAMPLE 3

Formulations containing 0.268% sodium phosphate dibasic heptahydrate, 0.014% citric acid, 0.83% sodium chloride, with the pH adjusted to 7.3 in qs water, and the amounts of bimatoprost, BAK, and EDTA listed in Table 3 below were prepared by conventional methods well known in the art.

TABLE 3

Formulations

| | |
|---|---|
| A. | 0.03% Bimatoprost (50 ppm BAK) - Control |
| B. | 0.015% Bimatoprost (50 ppm BAK) |
| C. | 0.015% Bimatoprost (50 ppm BAK) 0.03% EDTA |
| D. | 0.015% Bimatoprost (200 ppm BAK) |
| E. | 0.015% Bimatoprost (200 ppm BAK) 0.03% EDTA |
| F. | 0.015% Bimatoprost (50 ppm BAK) 0.015% EDTA |
| G. | 0.015% Bimatoprost (200 ppm BAK) 0.015% EDTA |
| H. | 0.015% Bimatoprost (125 ppm BAK) |
| I. | 0.015% Bimatoprost (125 ppm BAK) 0.03% EDTA |
| J. | 0.015% Bimatoprost (125 ppm BAK) 0.015% EDTA |
| K. | 0.015% Bimatoprost (150 ppm BAK) |
| L. | 0.015% Bimatoprost (150 ppm BAK) 0.1% EDTA |
| M. | 0.015% Bimatoprost |
| N. | 0.03% Bimatoprost |

EXAMPLE 4

The effect of benzalkonium chloride (BAK) and ethylene diaminetetraacetic acid (EDTA) on bimatoprost permeability across primary culture of rabbit corneal epithelial cell layers (RCECL) was studied. Corneal epithelial cells were harvested from New Zealand White rabbits and cultured on Transwell™ filters until confluency (Day 5). For the transport experiment, cells were first equilibrated in transport buffer for 1 hour at 37° C. Dosing solution containing 0.015% or 0.03% bimatoprost with varying concentrations of BAK and EDTA was then applied to the apical compartment of the Transwell™ (2 cultures; n=3-4 per culture) and the cells were incubated at 37° C. At 30, 60, 90 and 120 minutes postdose, 200 µL samples were taken from the basolateral chamber for apical to basolateral (AB) transport. The samples were analyzed by a liquid chromatography tandem mass spectrometry (LC-MS/MS) method with quantitation range of 1-600 ng/mL.

Figure 2:
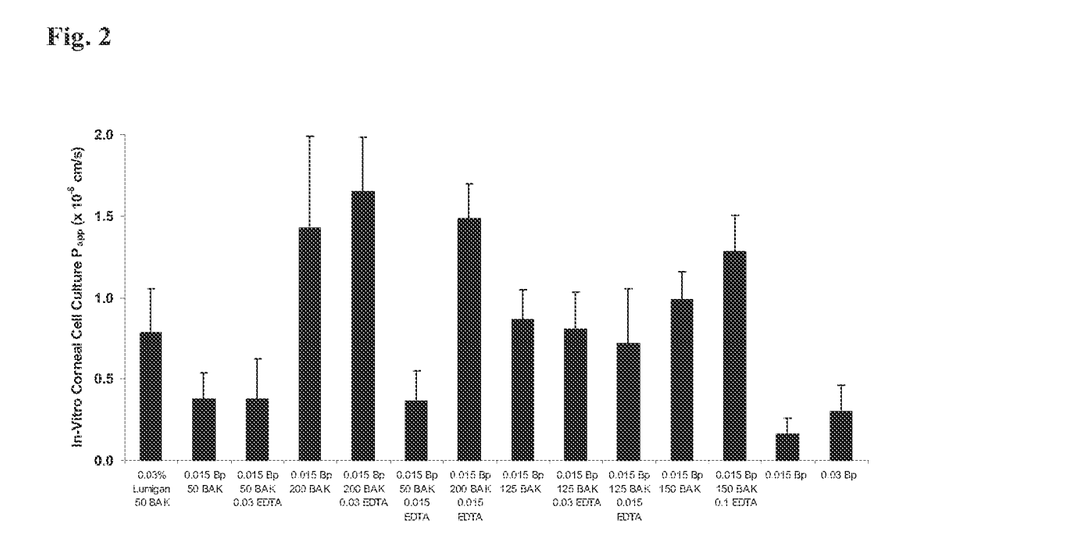
FIG. 2 is a plot showing the membrane permeability of bimatoprost in several different formulations.

The results are presented in FIG. 2.

EXAMPLE 5

A drop of formulation J (see Table 3) is administered once daily topically to the eye of a person suffering from glaucoma. After a few hours, intraocular pressure drops more and less hyperemia is observed than would be observed for formulation A. Lowered intraocular pressure persists for as long as the treatment continues.

EXAMPLE 6

Human patients were instructed to instill 1 drop of the study medication (Bimatoprost 0.01% ophthalmic solution, Bimatoprost 0.0125% ophthalmic solution or Bimatoprost 0.03% ophthalmic solution (LUMIGAN®) in each eye once-daily in the evening. Bimatoprost 0.01% ophthalmic solution contained bimatoprost 0.01%, benzalkonium chloride (BAK) 200 ppm, sodium phosphate dibasic heptahydrate, citric acid, sodium chloride, sodium hydroxide, hydrochloric acid, and purified water. Bimatoprost 0.0125% ophthalmic solution contained bimatoprost 0.0125%, BAK 200 ppm, sodium phosphate dibasic heptahydrate, citric acid, sodium chloride, sodium hydroxide, hydrochloric acid, and purified water. Bimatoprost 0.03% ophthalmic solution (LUMIGAN® (bimatoprost ophthalmic solution) 0.03% contained bimatoprost 0.03%, BAK 50 ppm, sodium phosphate dibasic heptahydrate, citric acid, sodium chloride, sodium hydroxide, hydrochloric acid, and purified water.

Prior to initiation of study treatment, each patient who qualified for entry was assigned a study patient number that was used on all patient documentation. Within the series of patient numbers provided to the site, numbers were assigned in ascending order without omissions. Patients were assigned a treatment group based on a central randomisation schedule stratified by baseline (Day 0, Hour 0) IOP and prestudy CCT. Patients were placed into 1 of 6 strata as follows:

TABLE 4

| Stratum 1 | Stratum 2 | Stratum 3 | Stratum 4 | Stratum 5 | Stratum 6 |
|---|---|---|---|---|---|
| IOP High (>25 mm Hg) CCT Thin (<555 µm) | IOP High (>25 mm Hg) CCT Average (555-600 µm) | IOP High (>25 mm Hg) CCT Thick (>600 µm) | IOP Low (≤25 mm Hg) CCT Thin (<555 µm) | IOP Low (≤25 mm Hg) CCT Average (555-600 µm) | IOP Low (≤25 mm Hg) CCT Thick (>600 µm) |

Within each stratum, a patient was assigned through the automated Interactive Voice Response System/Interactive Web Response System (IVRS/IWRS) to either Bim 0.01%, Bim 0.0125%, or Bim 0.03° A (LUMIGAN®) once-daily in an even allocation (1:1:1) according to the schedule of randomization numbers prepared by Allergan. The automated IVRS/IWRS was used to manage the randomization and treatment assignment, and sites dispensed medication according to this system.

At baseline, no statistically significant differences in mean IOP were observed between each of the investigational treatments and LUMIGAN®. At Hours 0, 4 and 8, respectively, mean IOP (mm Hg) was [Bim 0.01%: 25.1, 23.0, 22.3; Bim 0.0125%: 25.1, 23.0, 22.4; LUMIGAN®: 25.0, 23.2, 22.3]. Mean IOP at follow-up ranged from 16.4 to 17.9 mm Hg for Bim 0.01%, 16.6 to 18.3 mm Hg for Bim 0.0125%, and 16.1 to 17.8 mm Hg for LUMIGAN®. Bim 0.01% was equivalent to LUMIGAN® for mean IOP. For the comparison of Bim 0.01% with LUMIGAN®, at 17/17 timepoints, the CIs (95% or 97.5% according to the Hochberg procedure) of the between-treatment difference were within ±1.50 mm Hg and at 9/17 timepoints were within ±1.00 mm Hg. For the comparison of Bim 0.0125% with LUMIGAN®, at 16/17 timepoints, the CIs (95% or 97.5% according to the Hochberg procedure) of the between-treatment difference were within ±1.50 mm Hg, at 2/17 timepoints were within ±1.00 mm Hg, and at 9/17 timepoints were within ±1.16 mm Hg.

Mean Change from Baseline IOP (non-inferiority/superiority at 1.50 mm Hg Margin)

At baseline, no statistically significant differences in mean IOP were observed between each of the investigational treatments and LUMIGAN®. At Hours 0, 4 and 8, respectively, mean IOP was [Bim 0.01%: 25.1, 23.0 and 22.3 mm Hg; Bim 0.0125%: 25.1, 23.0, 22.4 mm Hg; LUMIGAN®: 25.0, 23.2, 22.3 mm Hg].

All treatments studied showed statistically and clinically significant mean decreases from baseline IOP at all follow-up timepoints (p<0.001). Mean changes from baseline IOP ranged from −5.2 to −7.8 mm Hg for Bim 0.01%, −5.2 to −7.5 mm Hg for Bim 0.0125%, and −5.6 to −8.0 mm Hg for LUMIGAN®.

For the comparison of both Bim 0.01% and Bim 0.0125% with LUMIGAN®, at 15/17 timepoints, the upper limit of the 95% CI of the between-treatment difference was within the 1.50 mm Hg margin.

For 2 timepoints (Week 2/Hour 4, Month 6/Hour 4) the upper limit was >1.50 mm Hg favouring LUMIGAN® over Bim 0.01% (1.70 mm Hg; 1.53 mm Hg, respectively) and Bim 0.0125% (1.67 mm Hg; 1.75 mm Hg, respectively).

Bim 0.01% has an acceptable long-term safety profile with no areas of particular concern when administered once-daily for up to 12 months.

Bim 0.01% demonstrated an improved safety profile with a statistically significantly lower incidence of overall adverse events (p=0.010), ocular adverse events (p=0.005), overall treatment-related adverse events (p=0.016), and ocular treatment-related adverse events (p=0.016) when compared with LUMIGAN®.

LUMIGAN® (0.03% bimatoprost in 50 ppm BAK) has been shown to be both an effective and safe topical IOP-lowering medication. This 12-month study was designed to confirm that IOP-lowering efficacy can be maintained and the safety profile improved by lowering the concentration of the active ingredient and changing the formulation. This was achieved by increasing the concentration of the preservative BAK from 50 ppm to 200 ppm to ensure comparable ocular exposure to that achieved by LUMIGAN®. Two formulations of bimatoprost (Bim 0.01% and Bim 0.0125%, 200 ppm BAK) were selected for evaluation in this study. A previous paired-eye study of 4 formulations and LUMIGAN® demonstrated that Bim 0.01% (200 ppm BAK) had superior safety and similar efficacy to LUMIGAN® (192024-030). In the same study, Bim 0.015% (200 ppm BAK) also showed comparable efficacy to LUMIGAN® but had a similar incidence of ocular adverse events. For the purposes of the present phase 3 study, in addition to Bim 0.01%, a concentration of bimatoprost between 0.01% and 0.015% was chosen for investigation—bimatoprost 0.0125%.

Two primary endpoints were evaluated in this 12 month study. For US regulatory purposes, the primary efficacy endpoint was mean IOP at all timepoints up to and including the month 3 visit assessed using an equivalence analysis. For EU regulatory purposes, the primary endpoint was mean change from baseline IOP analysed using a strategy of non-inferiority and superiority.

All treatments in this study were effective in lowering IOP at all follow-up timepoints (p<0.001). Mean IOP ranged from 16.4 to 17.9 mm Hg for Bim 0.01%, 16.6 to 18.3 mm Hg for Bim 0.0125%, and 16.1 to 17.8 mm Hg for LUMIGAN® over all post-baseline timepoints. The primary analysis for US regulatory purposes at 3 months showed that the new formulation, Bim 0.01%, was equivalent in efficacy to LUMIGAN®. The 12 month results demonstrate that Bim 0.01% continues to meet the definition of equivalence. The 95% and 97.5% confidence intervals (CIs) of the between-treatment difference in mean IOP were within ±1.50 mm Hg at all (17/17) post-baseline timepoints and within ±1.00 mm Hg at 9/17 post-baseline timepoints. For the comparison of Bim 0.0125% with LUMIGAN®, at 16/17 timepoints, the 95% and 97.5% CIs of the between-treatment difference were within ±1.50 mm Hg, at 2/17 timepoints were within ±1.00 mm Hg, and at 9/17 timepoints were within ±1.16 mm Hg.

Mean change from baseline IOP was analysed for EU regulatory purposes. From comparable baseline IOP, mean IOP changes from baseline ranged from −5.2 to −7.8 mm Hg for Bim 0.01%, −5.2 to −7.5 mm Hg for Bim 0.0125%, and −5.6 to −8.0 mm Hg for LUMIGAN®. For the comparison of both Bim 0.01% and Bim 0.0125% with LUMIGAN®, at 15/17 timepoints, the upper limit of the 95% CI of the between-treatment difference was within the 1.50 mm Hg margin. For 2 timepoints (Week 2/Hour 4, Month 6/Hour 4) the upper limit was >1.50 mm Hg favouring LUMIGAN® over Bim 0.01% (1.70 mm Hg, 1.53 mm Hg, respectively) and Bim 0.0125% (1.67 mm Hg, 1.75 mm Hg, respectively). The PP analyses gave similar results to the ITT analyses.

Secondary non-inferiority analyses showed Bim 0.01% to be non-inferior to LUMIGAN® for mean IOP (in both the ITT and PP populations), mean diurnal IOP and change from baseline mean diurnal IOP. Bim 0.0125% did not meet the definition of non-inferiority for mean IOP. In addition, the single secondary analysis for the US regulatory review of mean diurnal IOP, showed Bim 0.01% to be equivalent to LUMIGAN®. Bim 0.0125% did not meet the definition of equivalence for this analysis.

A sensitivity analysis was performed on the PP population for US regulatory purposes. For the comparison of Bim 0.01% with LUMIGAN®, at 17/17 timepoints, the 95% CIs of the between-treatment difference were within ±1.50 mm Hg, at 6/17 timepoints were within ±1.00 mm Hg, and at 9/17 timepoints were within ±1.11 mm Hg. For the comparison of Bim 0.0125% with LUMIGAN®, at 17/17 timepoints, the 95% CIs of the between-treatment difference were within ±1.50 mm Hg, at 4/17 timepoints were within ±1.00 mm Hg and at 9/17 timepoints were within ±1.19 mm Hg.

The safety results showed an overall improved safety profile for Bim 0.01% and Bim 0.0125% compared with LUMIGAN®. An improved macroscopic hyperaemia safety profile was observed in the Bim 0.01% and Bim 0.0125% groups compared with the LUMIGAN® group as demonstrated by incidence of patients experiencing worsening in severity, at least one clinically significant change from baseline severity grade, peak severity changes from baseline and also in mean peak severity. Bim 0.01% consistently showed a superior profile to LUMIGAN® in the severity of macroscopic hyperaemia over the 12 month follow-up; the improvement over LUMIGAN® ranged from 20-30% in the mean peak change from baseline of severity (p=0.01).

Biomicroscopic examinations supported these observations. An increased severity of conjunctival hyperaemia was more commonly noted with LUMIGAN® (49.2%) than with Bim 0.01% (41.1%) or Bim 0.0125% (35.1%), and the LUMIGAN® group had consistently more patients with moderate/severe hyperaemia over the 12-month study period. Overall, Bim 0.01% showed an improved ocular surface tolerability compared with LUMIGAN®, as demonstrated by the low incidence of corneal abnormalities on the ocular surface. Punctate keratitis occurred in only 5 patients (2.7%) receiving Bim 0.01% compared with 11 patients (5.9%) receiving LUMIGAN®. These are reassuring findings given the 4-fold increase of BAK in the new formulation.

Overall adverse events, ocular adverse events, overall treatment-related adverse events, and ocular treatment-related adverse events were reported by a statistically significantly smaller percentage of patients in the Bim 0.01% and Bim 0.0125% groups compared with the LUMIGAN® group. No significant differences were seen between the test formulations. The majority of ocular adverse events and treatment-related adverse events were mild in severity. Conjunctival hyperaemia was the most frequently reported adverse event and was seen in a significantly smaller percentage of patients in the Bim 0.0125% group (26.6%) compared with the LUMIGAN® group (39.0%; p=0.010). The incidence of conjunctival hyperaemia in the Bim 0.01% group was 31.4%. There were no notable non-ocular adverse events and incidences were slightly higher in the Bim 0.01% (43.2%) and LUMIGAN® (41.2%) groups compared with the Bim 0.0125% (36.7%) group.

Patient's and physician's perceptions of all treatments were positive. The vast majority would have been very/extremely willing to use or prescribe the study treatment and most patients did not experience any change in eye appearance. This is an important finding as satisfaction with glaucoma medication is vital for compliance and continuation of treatment.

Conclusions

The 12-month results demonstrate equivalence of efficacy between the new formulation of bimatoprost (Bim 0.01%, BAK 200 ppm) and LUMIGAN® (Bim 0.03%, BAK 50 ppm) at all timepoints for mean IOP, and non-inferiority to LUMIGAN® at 15/17 timepoints for mean change from baseline IOP. Compared with LUMIGAN®, Bim 0.01% had significantly fewer adverse events (all causality and treatment-related). Furthermore, patients randomised to Bim 0.01% experienced less severe macroscopic hyperaemia, significantly fewer ocular adverse events and significantly fewer discontinuations due to ocular adverse events.

What is claimed is:

1. A method of lowering intraocular pressure in a person with glaucoma or ocular hypertension, the method comprising administering once daily to an eye of the person a first composition comprising about 0.01% w/v bimatoprost and about 0.02% w/v benzalkonium chloride, wherein the method lowers intraocular pressure as effectively and results in improved ocular surface tolerability as compared to the once daily administration of a second composition comprising 0.03% w/v bimatoprost and 0.005% w/v benzalkonium chloride.

2. The method of claim 1, wherein the first composition has a pH of about 7.3.

3. The method of claim 1, wherein the first composition comprises 0.01% w/v bimatoprost and 0.02% w/v benzalkonium chloride.

4. The method of claim 2 wherein the first composition has a pH of 7.3.

5. The method of claim 1 wherein the first composition results in less punctate keratitis as compared to the second composition.

6. The method of claim 1 wherein the first composition results in less hyperemia as compared to the second composition over a 12 month period.

7. The method of claim 1 wherein the first composition results in less macroscopic hyperemia as compared to the second composition.

8. The method of claim 1 wherein the first composition results in less moderate/severe hyperemia as compared to the second composition.

9. The method of claim 1 wherein the first composition is further comprised of sodium phosphate heptahydrate, citric acid monohydrate and water.

10. The method of claim 1 wherein the first composition is further comprised of sodium phosphate heptahydrate, citric acid monohydrate, water, sodium chloride and hydrochloric acid and sodium hydroxide to adjust the pH.

11. The method of claim 1 wherein the method results in less overall adverse events, ocular adverse events, overall treatment-related adverse events and ocular treatment-related adverse events as compared to the once daily administration of a second composition comprising 0.03% w/v bimatoprost and 0.005% w/v benzalkonium chloride.

12. The method of claim 10 wherein the first composition is further comprised of about 0.26% w/v dibasic sodium phosphate heptahydrate and about 0.8% w/v sodium chloride.

* * * * *

UNITED STATES PATENT AND TRADEMARK OFFICE
CERTIFICATE OF CORRECTION

PATENT NO. : 9,155,716 B2  
APPLICATION NO. : 13/826047  
DATED : October 13, 2015  
INVENTOR(S) : Chin-Ming Chang et al.

Page 1 of 1

It is certified that error appears in the above-identified patent and that said Letters Patent is hereby corrected as shown below:

On the Title page, in item (63), in column 1, in "Related U.S. Application Data", line 5, delete "continuation" and insert -- continuation-in-part --, therefor.

On Page 2, in column 2, under "Other Publications", line 2, delete "Opthalmology," and insert -- Ophthalmology, --, therefor.

On Page 3, in column 1, under "Other Publications", line 57, delete "Opthalmology," and insert -- Ophthalmology, --, therefor.

On Page 3, in column 1, under "Other Publications", line 64, delete "Prostoglandins," and insert -- Prostaglandins, --, therefor.

On Page 4, in column 1, under "Other Publications", line 19, delete "Carbaminoyl-choline" and insert -- Carbamoyl-choline --, therefor.

On Page 4, in column 1, under "Other Publications", line 41, delete "Opthalmic" and insert -- Ophthalmic --, therefor.

On Page 4, in column 2, under "Other Publications", line 70, delete "Prostagladin" and insert -- Prostaglandin --, therefor.

In columns 3-4, in Table, line 5, delete "2.69" and insert -- 2.68 --, therefor.

In column 6, line 25, delete "(LUMIGAN®"" and insert -- (LUMIGAN®) --, therefor.

In column 6, line 51, delete "Bim 0.03° A" and insert -- Bim 0.03% --, therefor.

Signed and Sealed this  
Ninth Day of August, 2016

Michelle K. Lee  
*Director of the United States Patent and Trademark Office*